United States Patent
Nødskov

(10) Patent No.: US 6,975,908 B1
(45) Date of Patent: Dec. 13, 2005

(54) HANDHELD PIEZOELECTRIC ACUPUNCTURE STIMULATOR

(75) Inventor: Preben Nødskov, Rungsted Kyst (DK)

(73) Assignee: Medi-Direct UK Limited, West Bridgford (GB)

( * ) Notice: Subject to any disclaimer, the term of this patent is extended or adjusted under 35 U.S.C. 154(b) by 471 days.

(21) Appl. No.: 10/019,722

(22) PCT Filed: Jun. 30, 2000

(86) PCT No.: PCT/DK00/00355

§ 371 (c)(1),
(2), (4) Date: Jan. 2, 2002

(87) PCT Pub. No.: WO01/01920

PCT Pub. Date: Jan. 11, 2001

(30) Foreign Application Priority Data

Jul. 2, 1999 (DK) .................................. 1999 00251 U

(51) Int. Cl.⁷ ................................................ A61N 1/00
(52) U.S. Cl. ............................ 607/150; 607/2; 607/46; 607/145
(58) Field of Search .................... 607/1, 2, 46, 115, 607/145, 146, 150; 128/907

(56) References Cited

FOREIGN PATENT DOCUMENTS

| DE | 3121254 A1 | 12/1982 | | |
|---|---|---|---|---|
| DE | 4026820 A1 | 2/1992 | | |
| DE | 4026820 | * | 2/1992 | .......... A61H/39/08 |
| GB | 1446644 A | 9/1976 | | |

* cited by examiner

*Primary Examiner*—Angela D. Sykes
*Assistant Examiner*—Roderick Bradford
(74) *Attorney, Agent, or Firm*—Browdy and Neimark, P.L.L.C.

(57) ABSTRACT

In a handheld piezoelectric acupuncture stimulator with a pen-like, substantially electrically insulating exterior casing (1), at one end of which an actuator button (5) is mounted, while the other end is provided with a contact pin (9), which is connected with a first electrode of a piezoelectric converter, which by means of a spring-loaded impact hammer actuated by the actuator button (5) may be mechanically operated for generation of a high voltage electric pain relieving pulse with a low energy content, the piezoelectric converter with associated electrodes and said impact hammer with associated spring system are mounted in a common electrically insulating interior casing (8) designed for form-fit mounting in the exterior casing (1), whereby the electric connection between the second electrode of the piezoelectric converter and a contact ring (7) on the exterior casing comprises a leaf spring contact (10), which projects through the interior casing (8) and extends between said interior casing and the exterior casing (1).

3 Claims, 2 Drawing Sheets

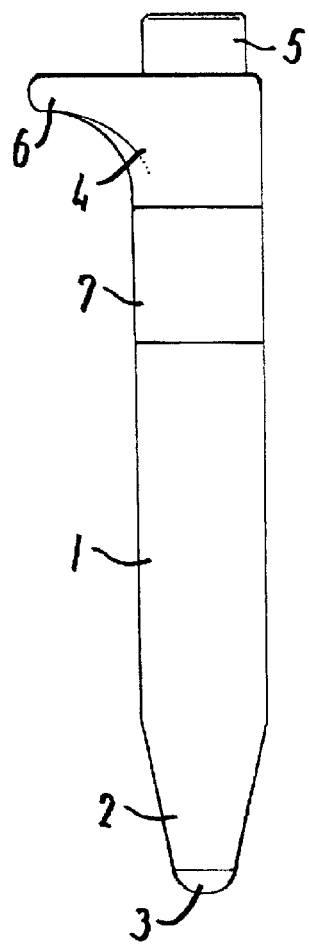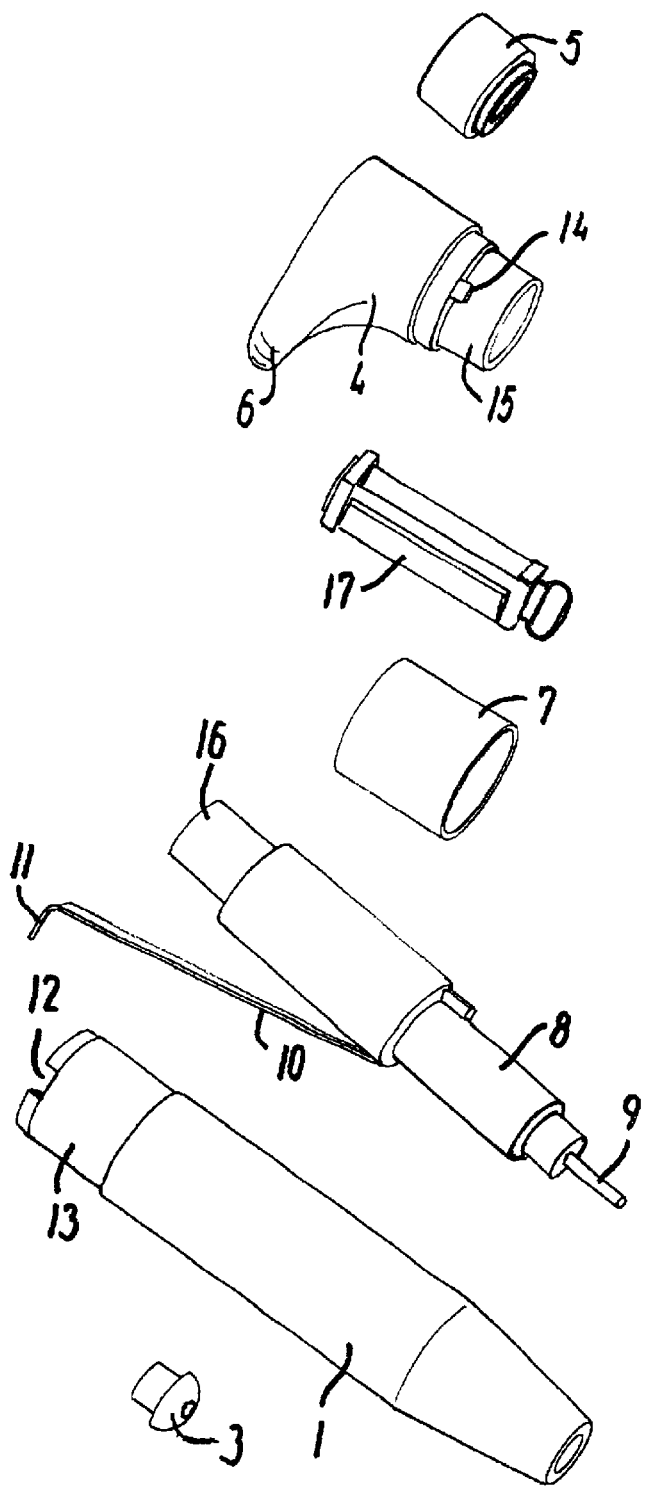
FIG.1
FIG.2

HANDHELD PIEZOELECTRIC ACUPUNCTURE STIMULATOR

REFERENCE TO RELATED APPLICATIONS

The present application is the national stage under 35 U.S.C. 371 of international application PCT/DK00/00355, filed Jun. 30, 2000, which designated the United States, and which international application was published under PCT Article 21(2) in the English language.

BACKGROUND OF THE INVENTION

1. Technical Field of the Invention

The present invention relates to a handheld piezoelectric acupuncture stimulator with a pen-like, substantially electrically insulating exterior casing, at one end of which an actuator button is mounted, while the other end is provided with a contact pin retracted from an end surface intended for contact with the skin in an acupuncture zone, said contact pin being connected with a first electrode of a piezoelectric converter, the second electrode of which is in electrical connection, on one hand, with a hand contact and is mechanically operable, on the other hand, by means of a spring-loaded impact hammer operated by the actuator button for generation of a high-voltage electric pain relieving pulse with a low energy content.

2. Prior Art

From DE-A1-40 26 820 an acupuncture stimulator of this kind is known, in which the piezoelectric converter and a comparatively long contact pin connected with its first electrode are arranged in their respective electrically insulating casings, surrounded by an electrically conductive metallic exterior casing and a likewise metallic treatment head with an end surface designed for contact with the skin, respectively. The impact hammer with accompanying actuator compression spring is accommodated in a bore in the comparatively elongate actuator button, while the return spring is mounted between recessed shoulder surfaces on the actuator button and an intermediate piece arranged around the piezoelectric converter between the actuator button and the insulating casing.

The considerable number of fairly small individual components in this known stimulator complicates its manufacture and mounting, and the design with an electrically conducting exterior casing and treatment head entails a less satisfactory insulation of the high-voltage electrode of the piezoelectric converter and may impair the efficiency of the stimulator.

OBJECT AND SUMMARY OF THE INVENTION

These drawbacks are remedied by the invention by a design of a stimulator of the kind defined, which is characterized in that the piezoelectric converter is mounted together with said first and second electrodes and said impact hammer with associated spring system, which comprises an actuator compression spring and a return spring, in a common electrically insulating interior casing designed for form-fit mounting in the exterior casing with said contact pin being retained with a comparatively short, protruding length at one end of the interior casing, at the other end of which a longitudinally displaceable impact hammer actuator is mounted, said actuator being mechanically connected with the actuator button, whereby the electric connection between the second electrode of the piezoelectric converter and said hand contact comprises a leaf spring contact, which projects through the interior casing and extends between said interior casing and the exterior casing for establishing contact with the hand contact, which is designed as a contact ring.

The leaf spring contact is preferably provided with a bent end portion fixed in a recess at the free edge of an end member of the exterior casing, said end member serving as a support for the contact ring. In this way it becomes possible in a simple manner by dimensioning the bent end portion of the leaf spring contact to obtain an accurate fixing of the spark distance between the end of the contact pin and the end portion of the stimulator intended for skin contact.

Owing to the fact that the handheld stimulator is designed for operation of the actuator button by the thumb, an accurate positioning of the exterior contact ring for establishing contact with the user's forefinger may be obtained by mounting the actuator button in a top member placed in extension of the exterior casing and the contact ring and having a protruding abutment as support for the user's forefinger knuckle, when the actuator button is operated by the thumb.

BRIEF DESCRIPTION OF THE DRAWINGS

The invention will now be explained in detail in the following with reference to the accompanying drawings, in which FIGS. 1 and 2 show an embodiment of a piezoelectric acupuncture stimulator according to the invention in mounted condition, and an exploded view of its main components, respectively.

DETAILED DESCRIPTION OF THE PREFERRED EMBODIMENT(S) OF THE INVENTION

Figure 3:
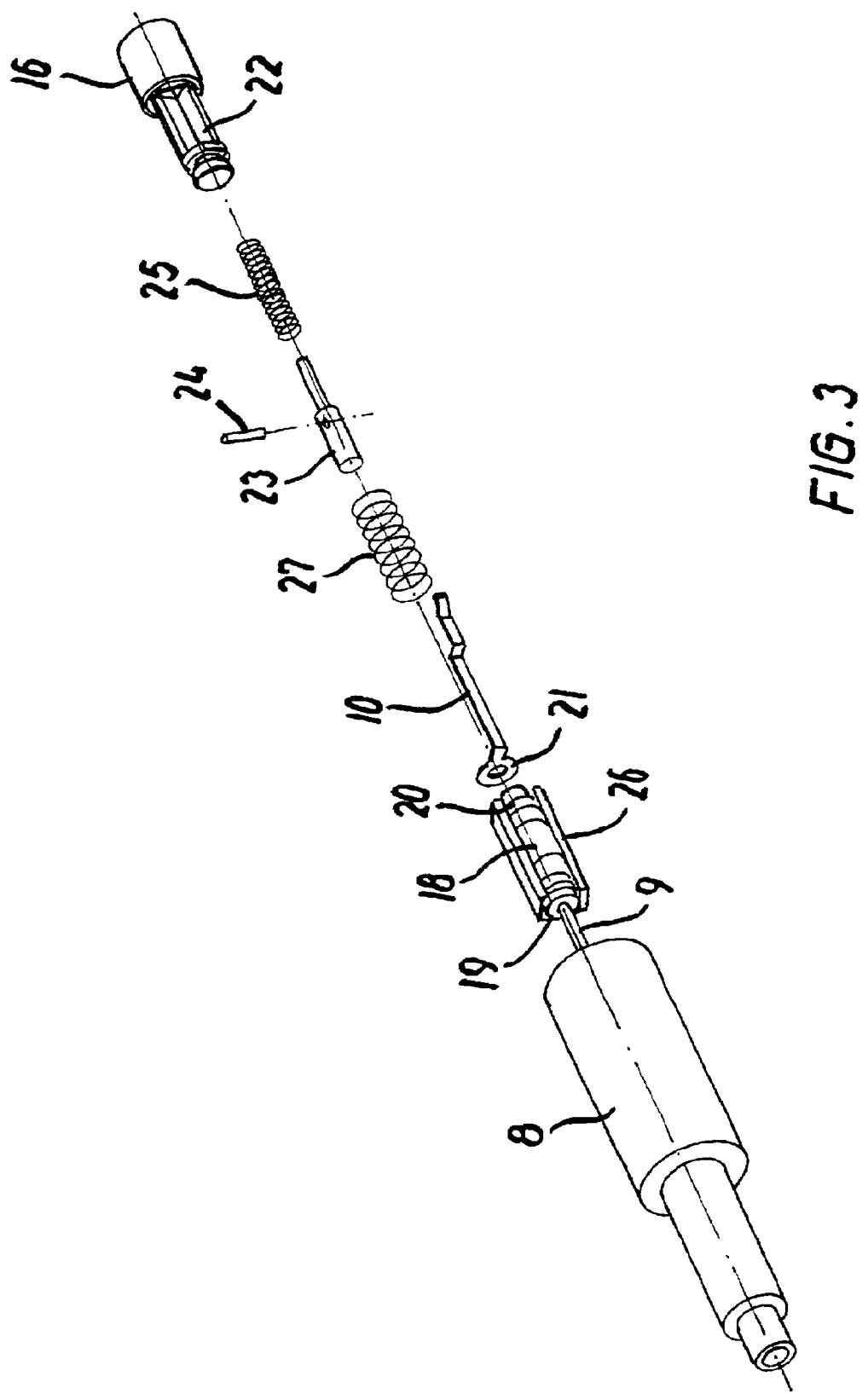
FIG. 3 shows more schematically the component parts mounted in the interior casing of the stimulator.

Seen from outside, the handheld piezoelectric acupuncture stimulator comprises, as shown in FIG. 1, an electrically insulating exterior casing 1 of a suitable plastics material, for instance nylon, with a substantially conical end portion 2 in connection with a treatment head 3 designed for contact with the skin in an acupuncture point.

At the opposite end, in extension of the exterior casing 1, a likewise electrically insulating top member 4 is provided, in which an actuator button 5 is mounted. Since the stimulator is designed for operation of the actuator button by the thumb, the top member 4 is designed with a protruding abutment 6, which during use is placed in abutment against the forefinger knuckle and thereby positions a contact ring 7 placed between the top member 4 and the exterior casing 1 in engagement with the user's forefinger.

The active components of the stimulator, which will be described below with reference to FIG. 3, are according to the invention, as shown in FIG. 2, mounted in an electrically insulating interior casing 8, from one end of which the contact pin 9 protrudes with a comparatively short length, said contact pin being adapted to transfer the pain relieving pulses produced by the stimulator by spark formation.

The interior casing 8 is designed for form-fit mounting in the exterior casing 1, the end of the contact pin 9 being somewhat retracted from the skin abutment formed by the treatment head 3 for determining a well-defined spark distance.

As likewise shown in FIG. 2, the electric connection between the earth electrode of the stimulator and the contact ring 7 is established by means of a leaf spring contact 10, which is passed through the interior casing 8 and extends between the interior casing and the exterior casing 1. The spring leaf contact 10 ends in a bent portion 11, which, for fixation of the position of the interior casing 8 in the, exterior casing 1, is brought into engagement with a recess 12 at the edge of an end portion 13 of the exterior casing 1 designed to support the contact ring 7. The bent end portion 11 of the leaf spring contact 10 is retained in the recess 12 by means of a protruding cam 14 on an end member 15 of the top member 4 adapted to be inserted into the end member 13.

At the opposite end of the interior casing 8 relative to the contact pin 9, a longitudinally displaceable actuator 16 is provided for the mechanical actuation of the piezoelectric converter. In the mounted condition, the actuator 16 is actuated by the actuator button 5 via a profiled pressure member 17 mounted in the top member 4.

The active components of the stimulator, which are mounted in the interior casing 8, comprise, as shown in FIG. 3, both the piezoelectric converter 18 with a first electrode 19 in connection with the contact pin 9 protruding from one end of the interior casing 8 and a second electrode 20 in electrical connection with a contact ring 21 provided at one end of the leaf spring contact 10, and the actuating mechanism designed for mechanical actuation of the converter 18, said mechanism comprising the longitudinally displaceable actuator 16 protruding from the opposite end of the interior casing 8 and having a guide 22 for an impact hammer 23 with a transverse blocking pin 24 and an actuator compression spring 25 and a return spring 27 positioned between the guide 22 and a holder 26 for the converter 18.

The mechanical function of the components shown in FIG. 3 is known per se and has the effect that by a longitudinal displacement of the actuator 16 in the interior casing 8 caused by operation of the actuator button 5, compression of the actuator compression spring 25 occurs at first, which spring by the release of the impact hammer 26 induced by the movement of the actuator with big force shoots the impact hammer towards the second electrode 20 of the converter 18. By the resulting instantaneous compression of the converter 18, the electrical pain relieving pulse with high voltage and comparatively low energy content is generated, for instance at 15,000 volt and 6 $\mu$A.

The pain relieving effect of the stimulator resides, as known per se, in that by the spark transfer of the pulse thus generated to an acupuncture point at the place, which is to be relieved from pain, an actuation of the body's own endorphin pain relieving system is supposed to take place.

What is claimed is:

1. A handheld piezoelectric acupuncture stimulator with a pen-like, substantially electrically insulating exterior casing (1), an actuator button (5) mounted at one end of the casing, a contact pin (9) retracted from an end surface (3), said contact pin provided at the other end of the casing, the contact pin intended for contact with the skin in an acupuncture zone, said contact pin being connected with a first electrode (19) of a piezoelectric converter (18), a second electrode (20) of the piezoelectric converter being in electrical connection with a hand contact (7) and being mechanically operable by means of a spring-loaded impact hammer (23) operated by the actuator button (5) for generation of high-voltage electric pain relieving pulse with a low energy content, characterized in that the piezoelectric converter (18) is mounted together with said first and second electrodes(19, 20) and said impact hammer (23) with a spring system, said spring system comprising an actuator compression spring (25) and a return spring (27), in a common electrically insulating interior casing (8) designed for form-fit mounting in the substantially electrically insulating exterior casing (1) said contact pin (9) being retained with a short, protruding length at one end of the interior casing (8), a longitudinally displaceable impact hammer actuator (16) being mounted at another end of the interior casing, said actuator being mechanically connected with the actuator button (5), whereby the electric connection between the second electrode (20) of the piezoelectric converter (18) and said hand contact (7) comprises a leaf spring contact (10), which projects through the interior casing (8) and extends between said interior casing (8) and the exterior casing (1) establishing contact with the hand contact (7) which is shaped as a contact ring.

2. An acupuncture stimulator according to claim 1, characterized in that the leaf spring contact (10) has a bent end portion (11) fixed in a recess (12) at the free edge of an end member of the exterior casing said end member serving as a support for the contact ring (7).

3. An acupuncture stimulator according to claim 1 or 2, characterized in that the actuator button (5) is mounted in a top member (4) placed in extension of the exterior casing (1) and the contact ring (7) and having a protruding abutment (6) as support for the forefinger knuckle of the user, when the actuator button (5) is operated by the thumb.

* * * * *